(12) United States Patent
Bahmanyar et al.

(10) Patent No.: US 11,813,045 B2
(45) Date of Patent: Nov. 14, 2023

(54) IMPLANTABLE INTRAVASCULAR PRESSURE SENSING APPARATUS AND METHOD OF OPERATING IT

(71) Applicant: IP2IPO INNOVATIONS LIMITED, London (GB)

(72) Inventors: Mohammad Reza Bahmanyar, London (GB); Christopher Neil McLeod, London (GB); Olive H Murphy, London (GB)

(73) Assignee: IP2IPO INNOVATIONS LIMITED, London (GB)

( * ) Notice: Subject to any disclaimer, the term of this patent is extended or adjusted under 35 U.S.C. 154(b) by 985 days.

(21) Appl. No.: 16/334,665

(22) PCT Filed: Sep. 20, 2017

(86) PCT No.: PCT/GB2017/052802
§ 371 (c)(1),
(2) Date: Mar. 19, 2019

(87) PCT Pub. No.: WO2018/055367
PCT Pub. Date: Mar. 29, 2018

(65) Prior Publication Data
US 2019/0343410 A1 Nov. 14, 2019

(30) Foreign Application Priority Data

Sep. 21, 2016 (GB) ...................... 1616090

(51) Int. Cl.
*A61B 5/0215* (2006.01)
*A61B 5/00* (2006.01)
(Continued)

(52) U.S. Cl.
CPC ........ *A61B 5/02158* (2013.01); *A61B 5/0031* (2013.01); *A61B 5/036* (2013.01);
(Continued)

(58) Field of Classification Search
CPC ... A61B 5/02158; A61B 5/0031; A61B 5/036; A61B 5/686; A61B 5/6861
See application file for complete search history.

(56) References Cited

U.S. PATENT DOCUMENTS

| 2004/0073137 A1* | 4/2004 | Lloyd | ..................... A61B 3/16 |
| | | | 600/561 |
| 2007/0118039 A1* | 5/2007 | Bodecker | ............. A61B 5/0215 |
| | | | 128/903 |

(Continued)

FOREIGN PATENT DOCUMENTS

| EP | 1837638 A1 | 9/2007 |
| WO | 20180055367 A3 | 3/2018 |

OTHER PUBLICATIONS

Office Action dated May 22, 2020 for Great Britain Patent Appl. No. GB1715278.6, 3 Pages.

(Continued)

*Primary Examiner* — Kaylee R Wilson
*Assistant Examiner* — Raymond P Dulman
(74) *Attorney, Agent, or Firm* — Maine Cernota & Curran

(57) ABSTRACT

An implantable intravascular pressure sensor comprising a first transducer arranged to provide a pressure dependent signal in response to alternating electrical signals of a first frequency band, a second transducer arranged to provide a reference signal in response to alternating electrical signals of a second frequency band different from the first frequency band and an antenna coupling for sending and receiving said signals.

10 Claims, 4 Drawing Sheets

(51) Int. Cl.
  *A61B 5/03*    (2006.01)
  *G01L 19/08*   (2006.01)
  *G01L 19/14*   (2006.01)

(52) U.S. Cl.
  CPC ............ *A61B 5/686* (2013.01); *A61B 5/6861* (2013.01); *A61B 5/6876* (2013.01); *G01L 19/086* (2013.01); *G01L 19/149* (2013.01); *A61B 2560/0247* (2013.01); *A61B 2560/0462* (2013.01); *A61B 2562/0219* (2013.01); *A61B 2562/04* (2013.01); *A61B 2562/12* (2013.01); *A61B 2562/162* (2013.01)

(56) References Cited

U.S. PATENT DOCUMENTS

| | | | |
|---|---|---|---|
| 2007/0282172 A1 | 12/2007 | Toumazou et al. | |
| 2009/0299216 A1* | 12/2009 | Chen .................. | A61B 5/031 600/561 |
| 2011/0036173 A1 | 2/2011 | Chommeloux et al. | |
| 2014/0275830 A1* | 9/2014 | Osorio ................ | A61B 5/0031 600/301 |
| 2014/0296687 A1* | 10/2014 | Irazoqui .............. | A61B 3/16 600/398 |
| 2016/0058324 A1* | 3/2016 | Cao .................... | A61B 5/7282 600/302 |

OTHER PUBLICATIONS

PCT Written Opinion for Appl No. PCT/GB2017/052802 dated Jan. 10, 2018, 12 pages.

* cited by examiner

IMPLANTABLE INTRAVASCULAR PRESSURE SENSING APPARATUS AND METHOD OF OPERATING IT

RELATED APPLICATIONS

This application is a national phase application filed under 35 USC §371 of PCT Application No. PCT/GB2017/052802 with an International filing date of Sep. 20, 2017 which claims priority of GB Patent Application 1616090.5 filed Sep. 21, 2016. Each of these applications is herein incorporated by reference in their entirety for all purposes. This application is related to PCT Application No. PCT/GB2017/05280 with an International filing date of Sep. 20, 2017 which claims priority of GB Patent Application 1616096.2 filed Sep. 21, 2016; PCT Application No. PCT/GB2017/052804 with an International filing date of Sep. 20, 2017 which claims priority of GB Patent Application 1616091.3 filed Sep. 21, 2016; PCT Application No. PCT/GB2017/052834 with an International filing date of Sep. 21, 2017 which claims priority of GB Patent Application 1616092. 1 filed Sep. 21, 2016; and PCT Application No. PCT/GB2017/053313 with an International filing date of Nov. 2, 2017 which claims priority of GB Patent Application 1618508.4 filed Nov. 2, 2016; each of these applications is herein incorporated by reference in their entirety for all purposes.

FIELD

The present invention relates to methods and apparatus for transducers, more particularly for transducers for implantation into a body, more particularly for implantation into a living human or animal body, for example into a lumen such as a vascular lumen.

BACKGROUND

Acoustic wave devices, such as Surface Acoustic Wave (SAW) and Bulk Acoustic Wave (BAW) devices can be used to provide transducers. SAW devices have been known for nearly three decades with their main applications being in signal processing for telecommunications and more recently as remote sensors in the automotive industry.

It has been proposed to measure intravascular pressure using implantable BAW or SAW devices for long term clinical monitoring. This may be beneficial because, where there is a need for long-term monitoring of patients the repeated use of invasive measurements increases risk and can ultimately lead to the physician deciding that such a procedure is too risky to undertake.

Implantable sensors offer an alternative to the problems of existing blood pressure measurement techniques set out above, for example. Once implanted, they can provide information over a long period without further risk each time they are used. Communication with the implant can be achieved through inductive coupling or through a radio-frequency link from a transmitter/receiver located outside the patient's body.

U.S. Pat. No. 6,206,835 describes the use of SAW device whose characteristic impedance is altered by a variable-capacitor type of pressure transducer which loads the SAW. Another approach is disclosed in U.S. Pat. No. 5,702,431, in which an implanted battery-powered circuit is recharged using inductive coupling. U.S. Pat. No. 6,539,253 describes the use of SAW filters in implants; the great stability and high Q-factor of the SAW devices are said to be advantageous in the design of the electronics.

WO2005058166 discloses an implantable, or wearable sensor for monitoring parameters, such as pressure, temperature, viscosity, or flow rate within a human or animal body. This document discloses a method of monitoring a parameter of a human or animal body wherein a surface acoustic wave device is implanted therein or attached thereto, wherein the device comprises a pair of interdigitated transducers spaced apart over the surface of a piezoelectric substrate, that is exposed to the parameter, wherein an antenna is connected to one of the interdigitated transducers, wherein a radio-frequency signal is supplied externally of the body to the antenna, is transmitted over the substrate surface to the other of the transducers, reflected therefrom back to the said one of the transducers and transmitted from the antenna thereof to a receiver, whereby comparison of the supplied and received signal provides a measurement of the parameter.

Wireless communication with a device which is surrounded by an electrically conductive medium, such as blood or human tissue, is challenging. The tissue may attenuate the signal to such an extent that the communication is compromised or prevented. This problem is still further exacerbated if there is a desire to transfer electrical power with the wireless communication. These problems may require the transmission of high signal power if any communication and/or power transfer is to take place. To protect the health of subjects there is a need to comply with regulations which set limits on the specific absorption of radiation (SAR) of the body. In the circumstances of long term monitoring there may be a need to take into account the habitual nature of exposure to radio signals.

SUMMARY

Aspects and embodiments of the present disclosure aim to address at least some of these drawbacks. Aspects and embodiments are set out in the appended claims. These and other aspects and embodiments are also described herein.

Described herein is an implantable intravascular pressure sensor comprising: a first transducer arranged to provide a pressure dependent signal in response to alternating electrical signals of a first frequency band; a second transducer arranged to provide a reference signal in response to alternating electrical signals of a second frequency band different from the first frequency band; and an antenna coupling for sending and receiving said signals. Since each transducer is arranged to respond to electromagnetic signals in different frequency bands, each transducer can be individually interrogated by choosing the corresponding frequency band of an excitation signal transmitted to an antenna of the pressure sensor.

Optionally, the antenna coupling is coupled to the first transducer and to the second transducer for coupling both transducers to the same antenna.

Optionally the pressure dependence of the response signal provided by the first transducer is associated with a pressure dependent change in a resonance characteristic of the first transducer. Moreover, the second transducer may be arranged so that pressure dependent changes in the resonance characteristic of the second transducer are less than those of the first transducer. For example, the second transducer may be wholly or partially insensitive to pressure changes. Resonance characteristics, such as frequency shifts and timing delays, are easy to measure with a high degree of accuracy. By arranging the device so that the two transducers respond by a different amount to pressure changes, differences between the responses of the two transducers can be used to determine fluid pressure of the environment in which the device is located.

The first transducer and the second transducer may be electrically in parallel with each other. The two transducers may be tuned (have a frequency response) selected so that the two transducers can operate independently of one another. That is to say that the presence of the first transducer has very little effect on the operation of the second transducer when the system is provided with alternating electrical signals within the second frequency band, and vice versa.

The device may further include an antenna coupled to the antenna coupling, the antenna being adapted for sending and receiving said signals, for example wherein the alternating electrical signals comprise radio frequency (RF) signals. By providing the device with an antenna, the ability of the device to receive electromagnetic signals is improved. The antenna may have a bandwidth which encompasses the first frequency band and second frequency band. This allows the antenna to preferentially receive electromagnetic signals having frequencies corresponding to each of the first and second frequency bands.

In addition, the pressure dependence of the response provided by the first transducer may be associated with deflection of a deflectable member by changes in intravascular pressure; and the reference response may be associated with a reference member arranged to be deflected less than the deflectable member by those same changes in intravascular pressure. Determination of pressure changes by measuring deflections provides a convenient means of determining changes in pressure while minimising the need for active electrical components, or complex moving parts.

The reference member and the deflectable member may comprise the same material. Moreover, the material from which each member is made may be crystalline. In particular, the reference member and the deflectable member may have the same crystal orientation, for example wherein the reference member and the deflectable member have the same crystal plane orientation. Comparison of readings between the two transducers is simplified when they are associated with deflections of the same material. Similarly, ensuring that the crystal plane orientation of the reference and deflectable members is the same helps to simplify the comparison of the two readings. In particular, when temperature of the device changes thermal expansion is prone to occur. In this case, ensuring that the reference and deflectable members are made from the same material, and even have the same crystal plane orientation, also ensures that the two members are affected equally by the thermal expansion, and therefore comparisons between the pressure dependence of the two signals can help to account for thermal effects.

The reference member and the deflectable member may be provided by different regions of the same substrate. This may provide an easy way to ensure that the two members are made from the same material, and/or that they have the same crystal plane orientation.

The different deflectability of the reference member and the deflectable member may be associated with at least one of: (a) different thicknesses of the substrate; and (b) arrangement of support of the substrate. For example, the arrangement of support may comprise a length of the substrate extending from a support, for example a length of substrate extending between two or more supports. Changing the support of the substrate to change its deflectability may be preferred as the support can be designed to achieve the desired deflectability in each region, without requiring the deflectable and reference members to be altered directly. This improves the freedom of design of the deflectable and reference members.

Similarly, the thickness of the substrate may be different in different parts of the substrate if the substrate tapers in thickness. Alternatively, the thickness of the substrate may change in a step-like manner. Changes in thickness may be achieved as part of the manufacturing process, for example by introducing etching steps to the manufacturing process.

Optionally, the deflectable member is coupled to an enclosed cavity that provides a reference pressure, whereby the deflectable member is deflected as the cavity is compressed or expanded in response to changes in intravascular pressure. By providing an enclosed cavity, the deflectable member can be arranged to deflect into and out of a controlled environment. Providing a controlled environment in this way can simplify the interpretation of measurements taken as described herein.

The deflectable member may at least partially enclose said cavity, for example wherein the deflectable member is provided by a membrane, for example wherein the membrane has a thickness of less than 200 μm, for example less than 60 μm, for example more than 5 μm, for example more than 10 μm, for example more than 20 μm, for example less than 100 μm, for example less than 60 μm. A thin membrane will deflect more due to the same pressure, resulting in a greater detectable change. Too thin, however, and the membrane will be mechanically fragile, risking a breakage of the entire device. The inventors have performed extensive experiments, and have determined that the above ranges are suitable for satisfying these two conflicting requirements.

The two transducers may each comprise an assembly of conductive elements and the frequency band in which the transducers respond is selected by the spatial arrangement of said conductive elements. Using geometrical factors such as spatial arrangements to tune the transducers to a particular frequency band may be desirable, as the spatial arrangement is unlikely to change with wear and tear, making the device more stable over long time periods, as well as providing a simple way to produce a plurality of devices which are highly consistent with one another.

The first transducer and the second transducer may comprise interdigitated transducers IDTs on a surface of a piezoelectric crystalline substrate. Moreover, the IDTs may both be oriented based on the crystal plane orientation of the substrate, for example wherein the crystal plane orientation of both IDTs is the same. IDTs provide a convenient way of measuring the physical and mechanical properties of a piezoelectric substrate. Orienting both IDTs in the same direction relative to the substrate crystal plane orientation may simplify the analysis of measurements.

The transducers may comprise conductive elements, which are arranged to provide at least one capacitor. Moreover, the conductive elements may be arranged to provide an LCR circuit. Such circuits may be beneficial as a matching circuit and/or may determine the frequency band associated with each transducer.

Also described herein is a method of reading an intravascular pressure sensor, the method comprising: obtaining a test response from the intravascular pressure sensor, wherein the test response is caused by receipt of a test signal by the intravascular pressure sensor; obtaining a reference response from the intravascular pressure sensor, wherein the reference response is caused by receipt of a reference signal by the intravascular pressure sensor, and; comparing the test response to the reference response to determine an indicator of intravascular pressure; wherein the test signal comprises a test frequency band and the reference signal comprises a reference frequency band, different from the test frequency band. Using this method, two separate responses can be obtained from the pressure sensor, by selecting an appropriate frequency band.

Comparing may comprise comparing at least one of: (i) a frequency characteristic; and (ii) the timing; of the test response to a corresponding feature of the reference response.

Frequency and timings may both be measured to a high degree of accuracy, and consequently may improve the resolution of the comparison.

The test response may comprise an alternating electrical signal within the test frequency band, and the reference response may comprise an alternating electrical signal within the reference frequency band. This improves the ease with which the test response may be obtained, since the test signal may be supplied by the same piece of equipment which subsequently receives the test response, without altering the arrangement of that piece of equipment. Similarly, this improves the ease with which the reference response may be obtained, since the reference signal may be supplied by the same piece of equipment which subsequently receives the reference response, without altering the arrangement of that piece of equipment.

Optionally, the intravascular pressure sensor is configured so that the test response is more dependent on intravascular pressure than the reference response. This provides a comparison of the two responses to be made in a convenient manner. The reference response may be used as a control to account for signal variations due to contributions other than pressure to the response of the intravascular pressure sensor. In particular, said variations may be associated with issues such as temperature, and ageing of the sensor. This allows for the comparison to adjust for changing temperatures of the environment in which the pressure sensor is located.

The intravascular pressure sensor may comprise the apparatus described above.

The method described herein may further comprise providing the reference signal and the test signal for transmission to the intravascular pressure sensor. Additionally, the bandwidth of the test signal may be wider than and encompasses a frequency band associated with the test response of the pressure sensor. Similarly, the bandwidth of the reference signal may be wider than and encompasses a frequency band associated with the reference response of the pressure sensor. The frequency band of the reference signal may be different from the frequency band of the test signal. Separating the frequency bands in this way, and allowing each signal to encompass its respective response simplifies the process of supplying and receiving the signals and responses respectively.

Also described herein is a controller for a reader device configured to transmit and receive radio frequency signals via an antenna, wherein the controller is configured to perform the method described above.

Also described herein is a reader device for reading an intravascular pressure sensor, the reader comprising: the controller described above; a signal provider configured to provide an alternating electrical signal for transmission to the intravascular pressure sensor; and a signal obtainer for obtaining response signals received from said intravascular pressure sensor.

The controller may be configured to control the reader device for sending the test and reference signals via the antenna. The controller may further be configured to obtain the test and reference responses via the antenna. The reader device may further comprise the antenna. At least the antenna may be carried by a garment, for example wherein the antenna is integrated into the garment, for example wherein the garment consists essentially of the antenna, or is formed as a wearable garment or accessory. This allows the reader device (or at least the antenna) to be situated close to a human or animal body for long periods without inconveniencing the user.

The signal provider may be configured to provide an alternating electrical signal suitable for providing electrical energy to the intravascular pressure sensor when implanted in a human or animal body. The implanted device could therefore be arranged to operate indefinitely, as there is no requirement for on-board energy sources.

Also described herein is a computer program product, comprising program instructions configured to program a processor to perform the method described above and/or to provide the controller for a reader device as described and/or claimed herein.

BRIEF DESCRIPTION OF THE DRAWINGS

Aspects and embodiments will now be described, purely by way of example, with reference to the accompanying drawings, in which.

DETAILED DESCRIPTION

Figure 1:
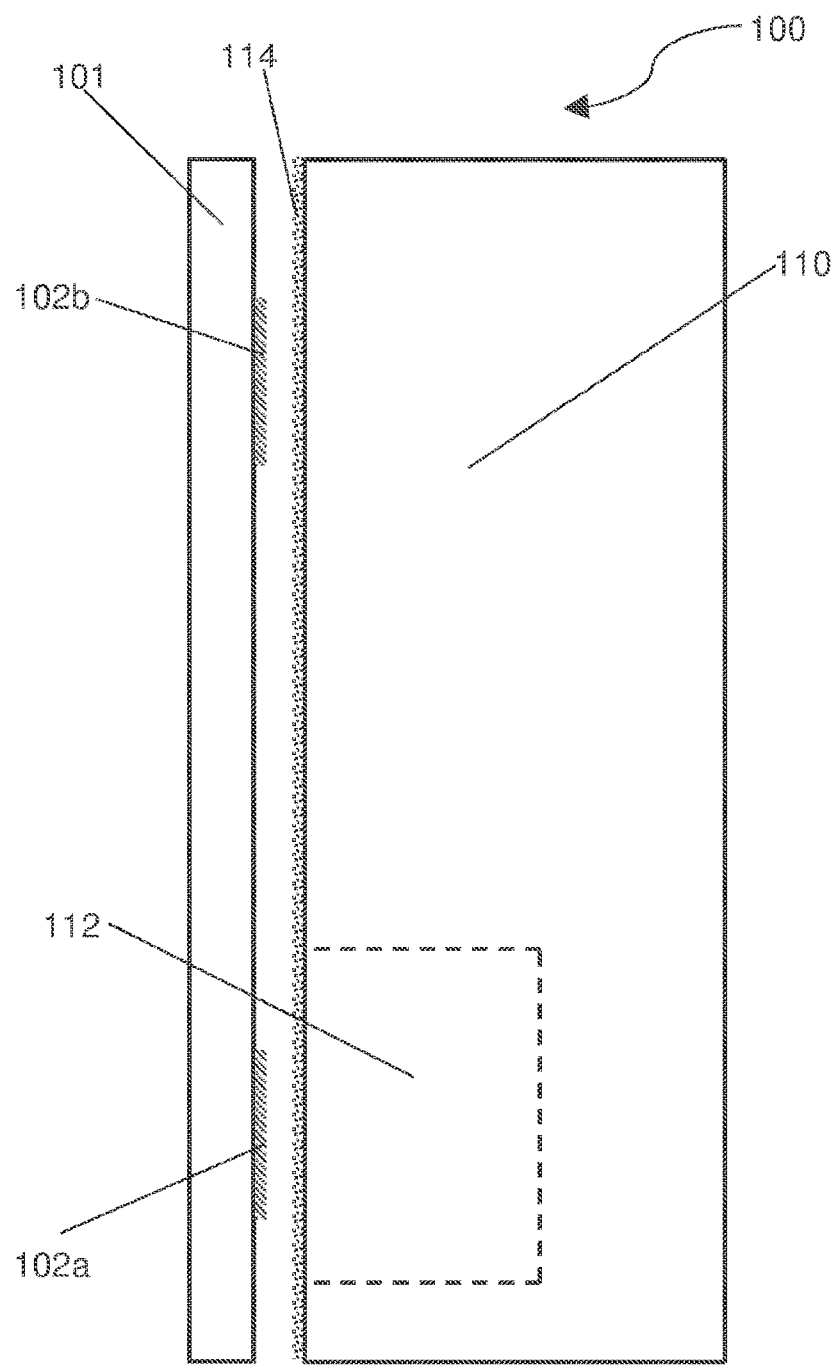
FIG. 1 shows a side elevation of an implantable intravascular device.

FIG. 1 shows an implantable device 100 comprising a first transducer 102a arranged to provide a pressure dependent signal in response to alternating electrical signals of a first frequency band. The device 100 also comprises a second transducer 102b arranged to provide a reference signal in response to alternating electrical signals of a second frequency band different from the first frequency band.

As one example, these transducers 102a, 102b, may comprise interdigitated transducers, IDTs, in which the frequency response is determined by the pitch of the IDT. Such transducers may comprise interdigitated conductive fingers disposed on a surface of a piezoelectric substrate. The frequency response of an IDT may also be affected by the mechanical stress and/or strain placed on the substrate.

As another example, these transducers 102a, 102b, may comprise bulk acoustic wave resonators. In bulk acoustic wave resonators, the transducers maybe provided by conductive film electrodes deposited on the first and second major surfaces of a membrane comprising a piezo electric substrate. The frequency response of such a transducer is determined, at least in part, by the spacing between the conductive film electrodes (e.g. the thickness of the membrane) and also by the mechanical stress and/or strain placed on the membrane.

FIG. 1 explains one particular way in which the different pressure dependence of the two transducers can be provided, but other constructions are envisaged.

In the example illustrated in FIG. 1, the device 100 comprises a membrane 101 upon which at least one assembly of components 102 is carried. In this example, the at least one assembly of components comprises two assemblies, the first transducer 102a, and the second transducer 102b. The first transducer 102a and the second transducer 102b are carried on the membrane.

The device 100 also comprises a body 110, arranged to be joined to the membrane by a hermetic bond 114 between the upper surface of the body 110 and the lower surface of the membrane 101. The body includes a cavity 112 extending from its upper surface towards the lower surface of the body, but not penetrating entirely through the body 110. When assembled, a hermetic bond 114 ensures that the cavity 112 is isolated from the environment exterior to the implantable device 100.

In FIG. 1, the membrane 101 and body 110 are shown separate from one another for clarity. However, when assembled, the membrane 101 is attached to the upper surface of the body 110 by the hermetic bond 114. The hermetic bond 114 also ensures that the cavity 112 is isolated from the external environment. For example, the cavity 112 may contain gas at a reference pressure which may be preselected (e.g. selected during manufacture, or otherwise prior to deployment), and the hermetic bond 114 is provided to seal the cavity 112 and inhibit variations in this pressure. This is important because if gas enters or escapes the cavity then the pressure is no longer known, and the device may need recalibrating or replacing. When sealed as described above, both components 102 of the assembly are contained within the hermetic bond 114, and are thus isolated and protected from the external environment.

The transducers 102a, 102b provided by the assembly 102 may be at least partially enclosed between the body 110 and the membrane 101, providing protection from the external environment. Moreover, in some embodiments, one or more parts of the assembly 102 may be located on the outside of the device, in contact with the external environment, so that comparative measurements may be made with reference to components located between the body 110 and the membrane 101.

When measuring fluid pressure, for example measuring intravascular pressure, the assembly 102 may measure this relative to a reference pressure in the cavity 112, for example by providing one or more pressure sensors as part of the assembly of components and comparing the external pressure to the pressure in the cavity.

A pressure measurement may be made using one or more interdigitated transducers (IDTs), which form part of the assembly of components. IDTs typically comprise a series of interlocking comb-shaped conductive elements (shown in more detail in FIG. 4). These can be arranged so that the membrane 101 or the body 110 provides a substrate for the one or more IDTs. In particular, one or more of the IDTs may be arranged to detect a deflection of the membrane as part of sensing the intravascular pressure. A specific arrangement may be that a first IDT is located in a first region of the membrane which is arranged to deflect due to changes in intravascular pressure more than a second IDT located in a second region of the membrane. For example, the first IDT may be disposed on a region of membrane which overlies the cavity, and may deflect into the cavity, compressing a gas in the cavity (wherein the amount and/or pressure of gas is already known). The second IDT may be disposed in a region of the membrane which is less easily deflected, for example it may be on a region which wholly or partially overlies the body and is rigidly coupled to it, e.g. in a region of the membrane which does not overly the cavity. This is described in more detail in reference to FIG. 2A.

These IDTs may be arranged to provide SAW devices, and may each operate either as "resonator" or "delay-line" devices. The function of "resonator" and "delay-line" type devices is explained below.

Whether implemented SAW IDTS, or BAW resonators, the conductive elements which make up the assemblies of components 102 may include one or more capacitors (not shown). Moreover, resistive and/or inductive elements (also not shown) may be included, to provide an LCR circuit to further help define the frequency range to which the assembly responds.

The membrane 101, and body 110 may comprise the same material, for example the material may be selected to reduce strains due to differential thermal expansion during the assembly process. This may mean that the membrane and the body may consist essentially of the same material, for example the same crystalline material. For example, the membrane and the body may both consist solely of the same material as each other. Moreover, this material may be a piezoelectric material such as quartz, since piezoelectric materials may be used as part of a surface acoustic wave (SAW) device, in combination with an IDT. It may be particularly advantageous to align each IDT with the same crystal direction of the substrate on which the IDT is provided. That is to say that the angle between the interlocked digits of the IDT and a particular crystalline axis is the same for each IDT.

While each of the membrane 101 and body 110 are shown as having approximately the same footprint (that is, having the same area in plan), this is not necessary, and one or other of these parts may extend beyond the other. For example, one of the components 102b may be situated between the body 110 and the membrane 101, while the other component 102a may be mounted on the membrane 101, but unsupported from below. This is equivalent to expanding the cavity 112 so that one end of the membrane 101 is not supported at all by the body 110.

The hermetic bond 114 may be formed in any suitable manner. In particular, a metal interlayer may be positioned between the body 110 and the membrane 101. The metal interlayer may form a diffusion bond such as a thermocompression bond, in which some of the metal interlayer diffuses into the crystal lattice of the body and the membrane, forming a hermetically sealed bond, for example a eutectic bond, in which an alloy, rather than an elemental metal, is used as the metallic interlayer. Specifically, the alloy is chosen to depress the melting point of the alloy, thus allowing a diffusion bond to be formed at a lower temperature. It will be appreciated in the context of the present disclosure that prior to bonding, a metal bond frame is formed on at least one of the substrates (e.g. on the membrane and/or the body. In case both body and membrane have metal bond frames, the bonding can done by thermocompression in which case no further interlayer (between the bond frames) needs to be used. In some possibilities a further interlayer can be used. This may comprise a metal of lower melting point that can form alloy with the bond frames. The adhesion of the bond frames to the substrates is usually enhanced by an adhesion layer (of different metal) that is deposited directly on the substrates before deposition of the bond frames.

Alloys suitable for such bonding may include a base material and a dopant. They may comprise, for example, a gold base material and a dopant. Base materials should have a good diffusivity in crystalline materials such as quartz and silicon. Gold is an example of such a base material. In some embodiments an adhesion layer comprising a material such as titanium or chromium may be applied between the crystalline material and the bond. This may be of particular utility where the crystalline material comprises quartz and the base material comprises gold. Suitable dopants contribute to the lowering of the melting temperature of the composition. Indium and tin are suitable examples of dopants for lowering the melting point of the eutectic composition. In particular, dopant levels of at least 15% by mass, at least 20% by mass, or even at least 25% by mass are suitable. Specifically, a doping level of 20% tin in gold, or a doping level of 27% indium in gold are suitable for the present application.

The hermetic bond 114 may be thick enough to support the membrane 101 so that the reference resonator 102b is held away from the surface of the base 110.

Figure 2A:
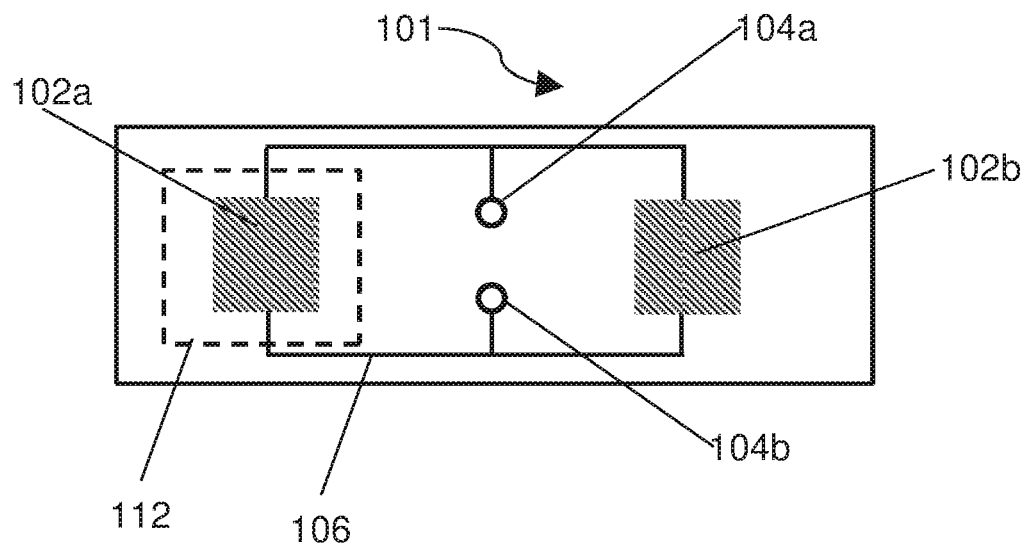
FIG. 2A is a plan view of part of an implantable intravascular device such as that illustrated in FIG. 1.

FIG. 2A shows an implantable intravascular device 100, which may have features such as those described above with reference to FIG. 1.

The device 100 includes a first transducer 102a and a second transducer 102b and an antenna coupling 104a, 104b. The first transducer 102a and the second transducer are arranged electrically in parallel with each other and with the antenna coupling 104a, 104b so that electrical signals from an antenna can be applied to both the first transducer 102a and the second transducer 102b.

The first transducer 102a and the second transducer 102b may each comprise interdigitated transducers, IDTs, on a substrate (such as the membrane 101 described above). These may be either "resonator" or "delay-line" type SAW devices. As such both may comprise an active IDT and either a reflector structure such as a plurality of "reflector lines"—an array of parallel lines of conductive material on the surface of the substrate. Such "resonator" and "delay-line" type devices will now be described in more detail.

It will be appreciated in the context of the present disclosure that surface acoustic waves can be formed on the surface of a piezoelectric substrate by applying alternating voltage to an IDT on that substrate. The wavelength of such a surface acoustic waves is set by the pitch of the IDT fingers, $\lambda$. Surface acoustic waves have a characteristic velocity, v, on such a surface. Thus by applying a voltage to the fingers of the IDT at the appropriate frequency, f, such that $v=f\lambda$, the voltage will generate surface acoustic waves. Energy is transferred onto the substrate (electrical energy input, mechanical energy stored in the waves), and the surface acoustic waves propagate across the surface of the substrate, perpendicular to the fingers of the IDT. For a "resonator" type device, the waves are reflected back across the surface of the substrate towards the IDT which generated them. This may be done by a tuned reflector (e.g. a series of reflector lines, such as lines of conductive material on the surface, with a pitch selected to reflect the SAW). It will be appreciated in the context of the present disclosure therefore that one possibility for a "resonator" type device is to have an IDT on a substrate with reflectors to either side of it, parallel to the IDT fingers.

The reflection on each reflector line is quite small, so each reflector may have at least one hundred lines, for example at least two hundred, for example at least 500. The energy of the surface acoustic wave will thus be contained in the mechanical vibrations of the surface between the reflectors. Stretching the surface of the substrate in a direction perpendicular to the IDT and reflector fingers will change the pitch of both the IDT and the reflectors so that the natural resonance frequency changes. This can be used as the basis of a strain- or pressure-transducer. The incoming electrical excitation, applied to the substrate by the active IDT is fairly close to the natural frequency of that IDT. A short pulse of excitation (typically 1 µs) generally provides a pulse bandwidth which is broad enough (typically 1 MHz) to cover the natural frequency of the IDT whether stretched or unstretched—other durations and bandwidths may be used. When the excitation pulse ends, the resonator will resonate only at its own natural frequency for a short time until the mechanical energy in the surface acoustic waves has been re-emitted as electrical energy from the IDTs.

For a "delay-line" device, the surface acoustic wave can be allowed to escape the immediate vicinity of the IDT and travel across the surface to one of: (i) a reflector; and (ii) another IDT. In the first case, the reflector will reflect the surface acoustic wave back to the source IDT. In the second case the other IDT converts the incoming surface acoustic wave to an electrical pulse at the frequency of the surface acoustic wave. A "delay-line" type device can be used as a strain or pressure transducer in either case.

In the case where a reflector is used, a short alternating voltage pulse is applied to the IDT (via electrical connections or an aerial); a short pulse of surface acoustic waves is emitted from the IDT and travels over the surface to the reflector. The reflector will reflect the surface acoustic wave back to the source IDT; a short electrical pulse is generated at the source IDT (for detection or transmission from the aerial). The double transit time (between the excitation pulse leaving the source IDT and the reflected pulse arriving back at the source IDT) gives a measurement of the strain or pressure, because both the speed of the surface acoustic wave and the distance travelled have a known relationship with surface stress and strain and hence with pressure. In the case where a second IDT is used, the excitation pulse travels over the surface to the second IDT. The second IDT converts the incoming SAW to a short electrical pulse.

The single transit time (between the excitation pulse leaving the source IDT and its arrival at the second IDT) gives a measurement of the distance travelled. Where resonator type devices are used, the reference transducer may be tuned so that its natural resonance frequency is different to that of the active resonator e.g. the transducer arranged to provide a pressure dependent signal. Generally the natural frequency of the active and reference transducers will be separated by at least 1 MHz, for example at least 2 MHz. As explained above, the reference transducer can be arranged on the substrate so as to be less sensitive to pressure than the active resonator—e.g. to be wholly or partially insensitive to pressure. Because it resonates at a different frequency its IDT can be connected in parallel with the IDT of the active resonator. The excitation signal can be tuned to each resonator independently, so we receive a return signal containing only one natural resonant frequency—either active or reference. This can enable the two signals to be compared to estimate pressure.

A membrane such as the membrane 101 shown in FIG. 1, may provide the substrate for these IDTs. The electrical components 102a of the first transducer are located on the membrane 101 such that when the device is assembled (which in this case comprises at least attaching the membrane 101 to the body 110), the first electrical components 102a will be located above the cavity in the body 110, the location of which is indicated by dashed line 112. By the same token, the second transducer 102b may be located on the membrane 101 such that when the device is assembled, is more rigidly supported by the body it is not located above the cavity 112.

The electrical components 102a, 102b may thus be arranged on a surface of the membrane 101, and connected together via electrical connections 106 in a parallel arrangement. Also connected to the electrical connections 106 are two couplings 104a, 104b for connecting an antenna to the electrical components 102a and 102b, also in a parallel configuration. The electrical components 102a, 102b may comprise the first transducer 102a, and the second transducer 102b. The first transducer is arranged to provide a pressure dependent signal in response to alternating electrical signals of a first frequency band, and the second transducer is arranged to provide a pressure dependent signal in response to alternating electrical signals of a second frequency band. The first and second frequency bands are different. The electrical components 102a, 102b may each comprise an active IDT and reflectors—for a "resonator" or "delay-line" as explained below. If the transducers comprise "delay-line" type transducers the components 102a, 102b may each comprise a source IDT which generates a surface acoustic wave and a receiving IDT which converts that surface acoustic wave to an electrical signal for transmission.

As shown, both transducers 102a, 102b, are connected to the same antenna couplings, but in some embodiments, each transducer may be connected to a different antenna. Where a single antenna is used, the bandwidth of the antenna may be sufficiently broad that a passband of the antenna encompasses the resonant frequency of both transducers 102a, 102b.

Although the two transducers are shown in a parallel arrangement with each other and with the antenna, embodiments exist in which some or all of these components are arranged in series with one another. This may be done in a variety of different ways. For example, significant signal loss may be acceptable, so a simple series circuit can be used. Alternatively, frequency selective bypass circuits may be placed in parallel with each transducer. The bypass circuit in parallel with the first transducer may be tuned to the frequency band of the second transducer, and the bypass circuit in parallel with the second transducer may be tuned to the frequency band of the first transducer.

In this way, even if the two are connected in series, the first transducer can be arranged to provide a pressure dependent signal in response to alternating electrical signals of a first frequency band and the second transducer can a reference signal in response to alternating electrical signals of a second frequency band different from the first frequency band. As will be appreciated by the skilled addressee in the context of the present disclosure, other electrical arrangements are possible.

Although the embodiment shown in FIGS. 1 and 2 does not include an antenna, some embodiments may be provided with one or more antennas for receiving RF signals, connected to the antenna couplings. Such an antenna may be arranged to operate at frequencies within a particular bandwidth. In particular this bandwidth may be chosen to encompass the first and second frequency bands, corresponding to the first and second transducers.

The transducers may be arranged to respond to pressure changes in their environment by detecting changes in the resonance characteristics of the transducer. For example, for sensing pressure external pressure may change the shape of the transducer assembly, which in turn may alter various measurable physical properties of each transducer. Such physical properties may include by way of example: resonance characteristics such as resonant frequency; speed of propagation of vibrations; physical separation of various components; and/or electrical properties. In particular, each transducer may be arranged to change its resonant frequency in response to pressure changes, or to introduce a pressure dependent time delay.

The two transducers may respond differently to pressure changes. For example, the change in a measurable physical property of the first transducer may be greater than the change in that same physical property of the second transducer. This may be achieved by one or more of: arranging the substrate of the transducers to respond differently, for example allowing the substrate of one transducer to distort more in response to pressure changes than the substrate of the other transducer; by mounting each transducer on a different substrate material, each material chosen to respond to pressure in a different manner. In some embodiments, where the substrate material is crystalline, such as quartz, it may be achieved by mounting the two transducers at different orientations relative to the crystal axes of the substrate upon which they are supported. This may provide a measure of temperature changes due to differential thermal expansion along the different crystal axes.

A particular example of a pressure dependent response is based on the degree to which part of the device can deflect due to pressure changes, that is providing a different degree of deflectability to different parts of the device. Specifically, this may include providing a deflectable member and a reference member in the device. As an example, the substrate of the first transducer 102a may comprise a portion of the membrane 101 located above the cavity 112 which may be able to deflect into the cavity. Just as part of the membrane may deflect to provide this pressure dependent response, any other type of deflectable member may also be used as a substrate. Likewise, the substrate of the second transducer 102b may comprise a portion of the membrane 101 which is less able to deflect in response to pressure changes. For example it may be more rigidly supported, for example by being carried on a shorter cantilever over the cavity 112, or by being carried on a part of the membrane which is more inhibited from deflecting by the body 110 of the transducer. Just as a portion of the membrane may be more rigidly fixed than the deflectable part to provide this reference response, any other type of reference member may also be used as a substrate. Typically the reference member and the deflectable member comprise the same material.

Additionally, or alternatively, a different deflectability of different portions of the device may be provided by altering the thickness of the substrate, or substrates comprising different materials, or providing different types of support for the substrates. In particular different types of cavity may be used to cantilever a part of the substrate out over a void to allow deflection of a portion of that substrate. For example the portion of the membrane may be carried between two supports with an gap between them beneath the membrane to provide the cavity. The dimensions of this gap between the supports and/or the type of support may be different for each transducer to provide the reference member and deflectable member as described above.

The cavity may be hermetically sealed from the external environment, and such a cavity may be filled with a gas. The deflectability of a membrane covering such a cavity can be selected by altering the pressure in the cavity (e.g. during manufacture or prior to implanting). In some embodiments, the reference pressure could be provided by filling the cavity with an elastic material. In any case, the general principle with such sealed cavities is that increases in external pressure cause one or more of the walls of the cavity to deflect into the cavity, compressing the gas in the cavity, and reductions in the external pressure cause one or more of the cavity walls to deflect out from the cavity, allowing the gas in the cavity to expand.

As a specific example, in the case where the transducers comprise IDTs, a change in the physical dimensions of the substrate on which the IDTs are supported may cause a change in the dimensions of the IDT. This in turn may change the separation of the interlocked digits, or other physical dimensions of the IDT, which may cause a change in the resonant frequency of the transducer. Additionally or alternatively, such a change in the physical arrangement of components may cause a pressure dependent time delay to be introduced into the measurement. For example, a transducer may comprise two IDTs; a source and receiver IDT. The measurement may comprise triggering the source IDT to emit a surface acoustic wave (SAW), and measuring the time delay until the receiver IDT receives the SAW. Such a system could also be provided using a single IDT and a reflector, wherein the IDT is triggered to emit a SAW, and measure the time delay for the SAW to reach the reflector, be reflected back towards the IDT, and be received by the IDT.

In either of the above cases, when the substrate has been deflected so that the IDT is on the convex surface, the time delay will be longer than it would be for an un-deflected substrate, as the path travelled by the SAW is longer than in the un-deflected case. Similarly, the distance between the interlocked digits of the IDT (the interdigital distance) becomes larger. Conversely, when the deflection is such that the IDT is on the concave surface, the surface on which the IDT is supported contracts and the path length and interdigital distance become shorter, this may be associated with a shorter time delay than in the un-deflected case. It will be appreciated by the skilled addressee in the context of the present disclosure that the surface with the IDTs on it is in tension when the external pressure is above the cavity pressure and under compression when the external pressure is below the cavity pressure The one or more walls of the cavity which deflect in this way can be selected by ensuring that those walls are more deflectable than the walls which are not intended to deflect in this way. For example, in FIG. 1 the membrane 101 is shown as being thinner than the other walls of the cavity 112, and so will deflect more than the other walls. In particular embodiments, the design may ensure that some of the walls do not deflect at all, or that the deflection of some walls is negligible compared with the deflection of other walls, when the external pressure changes. The membrane shown in FIGS. 1 and 2 may have a thickness of between 5 μm and 200 μm, for example, or more specifically between 10 μm and 100 μm, and in particular between 20 μm and 60 μm.

As described above, there are many ways in which the deflectability of part of the device may be altered, only one of which is to change the material from which different parts of the device are made. Some embodiments of the device may therefore be constructed substantially from a single material. In particular, the deflectable member and the reference material may be made from the same material. For example, as shown in FIGS. 1 and 2, the two transducers (each mounted on either the deflectable member or the reference member) are mounted on a single component. That is to say that the reference member and the deflectable member may comprise different portions of the same part of the device For example, in the example shown in FIGS. 1 and 2, the two members are different parts of the membrane 101.

A further development of this concept is that the reference and deflection members may have the same crystal plane orientation. In the case where the reference and deflection members are different portions of the same component, this may be easily achieved by forming the component (e.g. membrane 101) from a single crystal. Whichever method is used to achieve this, when the reference and deflection members have the same crystal plane orientation the two transducers may be provided such that they are each aligned with the same crystallographic direction simply by orienting the two transducers so that they are mounted on the substrate aligned with one another. Arranging the transducers in this way can help to ensure that the only differences between the output provided by the transducer associated with the reference member and the transducer associated with the deflectable member are due to the different responses of each transducer to pressure.

In particular, embodiments of the disclosure may control for the effect of temperature on the pressure measurement. For example, they may be arranged to compensate for the fact that an increase in temperature may cause a thermal expansion of some or all of the components. The reference and deflection members may be arranged to be equally affected by such changes in temperature, thereby thermal effects can be accounted for. For example, by ensuring that the reference and deflection members have the same orientation (with respect to the crystal axes of the substrate), any anisotropic thermal expansion effects can be controlled for. The benefit of this is further increased when the transducers themselves are also aligned with the same crystal direction. For example, the velocity of surface acoustic waves may depend on the propagation direction of those waves, and so the temperature coefficient of the velocity may also depend on propagation direction. The active and reference transducers may be aligned in the same direction, and a temperature sensor may be provided by providing a transducer which is aligned at a selected angle (say) 45° to the another and performing a differential measurement. It will thus be appreciated that the provision of a third transducer, aligned at a different angle to the other two (mutually aligned) transducers can provide two independent variable measurements—pressure and temperature together. This third transducer may be tuned to a different frequency band from the first and second transducers.

Figure 2B:
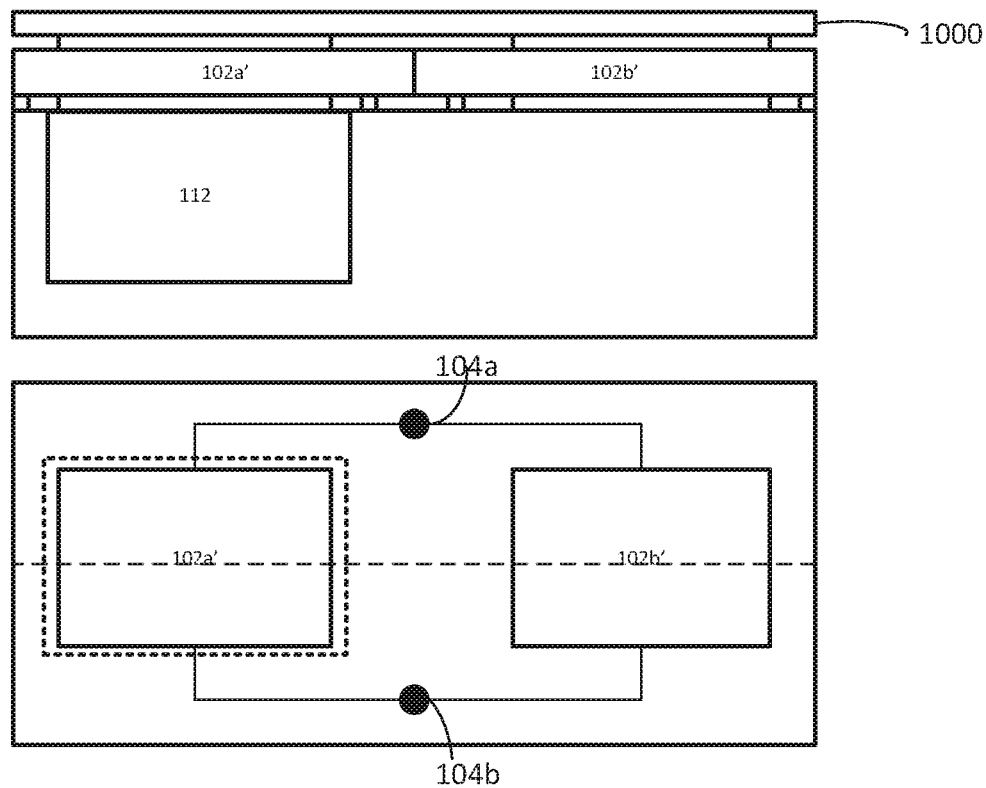
FIG. 2B includes a section view and a plan view of an implantable intravascular device such as that illustrated in FIG. 1.

FIG. 2B comprises a schematic view of a section through an implantable intravascular device, and a plan view of that same device.

This implantable device also comprises a first transducer 102a arranged to provide a pressure dependent signal in response to alternating electrical signals of a first frequency band, and a second transducer 102b arranged to provide a reference signal in response to alternating electrical signals of a second frequency band different from the first frequency band. The transducers 102a, 102b illustrated in FIG. 2B comprise bulk acoustic wave resonators.

In bulk acoustic wave resonators, the transducers maybe provided by conductive film electrodes deposited on the first and second major surfaces of a membrane. This membrane comprises a piezo electric material. The frequency response of such a transducer is determined, at least in part, by the spacing between the conductive film electrodes (e.g. the thickness of the membrane) and also by the mechanical stress and/or strain placed on the membrane. In addition, such transducers may comprise further conductive elements, in addition to the electrodes, which provide reactive impedance (such as capacitance and/or inductance). This reactive impedance can be selected to shift the resonant frequency of BAW transducers having the same type and thickness of substrate (membrane) between their electrodes.

The device 100 illustrated in FIG. 2B may include an acoustic isolation structure 1000, such as a Bragg reflector or a layer of gas trapped under a deformable covering to reduce the mass loading of the BAW resonators due to the presence of an intravascular fluid. As with the embodiment illustrated in FIG. 2A, an antenna coupling 104a, 104b can be provided for electrical connection of the transducers 102a', 102b' with an antenna. The first transducer 102a' and the second transducer 102b' are arranged electrically in parallel with each other and with this antenna coupling 104a, 104b so that electrical signals from an antenna can be applied to both the first transducer 102a' and the second transducer 102b'.

Whether by selecting the thickness of the membrane or by the provision of additional reactive impedance in the transducer, the reference BAW transducer may be tuned so that its natural resonance frequency is different to that of the active resonator e.g. the transducer arranged to provide a pressure dependent signal. Generally the natural frequency of the active and reference transducers will be separated by at least 1 MHz, for example at least 2 MHz. As explained above, the reference transducer can be arranged on the substrate so as to be less sensitive to pressure than the active resonator—e.g. to be wholly or partially insensitive to pressure. Because it resonates at a different frequency it can be connected in parallel with the test transducer. The excitation signal can comprise frequency components selected to excite each resonator independently, so we receive a return signal containing only one natural resonant frequency—either active or reference. This can enable the two signals to be compared to estimate pressure.

The transducers 102a', 102b' may carried on a membrane 101, and connected together electrically in parallel between two couplings 104a, 104b for connecting an antenna to the transducers 102a' and 102b'. As above, the first transducer is arranged to provide a pressure dependent signal in response to alternating electrical signals of a first frequency band, and the second transducer is arranged to provide a pressure dependent signal in response to alternating electrical signals of a second frequency band. The first and second frequency bands are different.

As shown, both transducers 102a', 102b', are connected to the same antenna couplings, but in some embodiments, each transducer may be connected to a different antenna. Where a single antenna is used, the bandwidth of the antenna may be sufficiently broad that a passband of the antenna encompasses the resonant frequency of both transducers 102a', 102b'.

As will be appreciated by the skilled addressee in the context of the present disclosure, other electrical arrangements are possible such as those described above for SAW transducer systems. Pressure sensitivity may also be provided in a similar way—e.g. by providing one BAW transducer on a reference member and another on a test member which is deflected more than the reference member by changes in intravascular pressure. The test member and reference member may be provided by different regions of the same membrane substrate as explained above.

The antenna coupling 104 of the embodiments described herein may comprise electrical and mechanical fixings for holding an antenna in place and electrically connecting it to the transducers 102a, 102b. Examples include vias at least partially through the body of the device, a trench for holding an antenna stem in place, and metallisation of one or more surface regions to provide conductive areas for connection to an antenna. Some examples of antenna couplings may include impedance matching circuitry and/or frequency selective structures such as filters.

Figure 3:
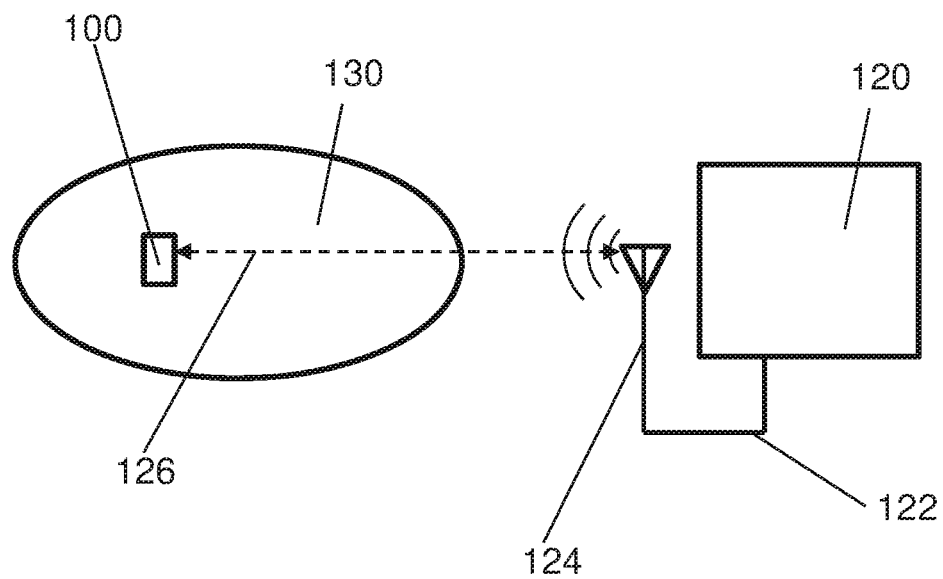
FIG. 3 shows a device such as that shown in FIG. 1 implanted in a body, and interacting with a reader.

Turning now to FIG. 3, there is shown an implantable device 100 such as that described above, and shown in FIGS. 1 and 2, implanted into a body 130. The body 130 may be a human or animal body, for example. Also shown in FIG. 3 is a reader device 120, the operations of which will be described in detail below. The reader device 120 is connected to a signal provider and receiver, shown here as antenna 124. A connection 122 is provided between the reader device 120 and the antenna 124 to allow communications signals to be transmitted between the reader device 120 and the antenna 124.

In operation, as shown, the reader device 120 provides signals to the antenna 124 via the connection 122. The antenna is arranged to output these signals as electromagnetic radiation, which is transmitted through the body 130 to the device 100, as shown by communications path 126. The device 100 receives the electromagnetic radiation, which triggers the device to respond with a pressure-dependent response, as described above. The response is transmitted back along the communications pathway 126, for example emitted as electromagnetic radiation which is received by the antenna 124. The antenna communicates the response to the reader device 120. Once the response is received, information can be extracted relating to the pressure in the environment surrounding the device 100.

Moreover, as described herein, two responses may be received; a test response and a reference response. These responses may relate, for example to a first signal provided by the first transducer, and a second signal provided by the second transducer. As described above, these may relate to a strongly pressure dependent result, and a result that is largely pressure independent. In this way the two results can be used together to determine the pressure in the location of the device, accounting for variations due to other factors, e.g. temperature.

The reader device may include a controller configured to perform the method steps set out below in respect of FIG. 5. For example, the controller may be configured to provide test and reference signals for sending to the device, and to receive test and reference responses. The controller may also include an analysis module to interpret the response signals, and determine a pressure in the environment of the sensor. This determination may make use of additional data stored in a memory associated with the controller, for example calibration data. The controller itself may comprise a hardware implementation, a software implementation or a combination of these.

As described above in more detail, the test and reference responses may be arranged to interrogate each of the first and second transducers of the device respectively. This may be achieved by arranging the first transducer to respond to frequencies in a first band, and arranging the second transducer to respond to frequencies in a second band, wherein the first and second frequency bands are different. In particular, the first and second bands may have no or only a negligible overlap with one another.

Moreover, the signal provider (for example the antenna) may be arranged to provide an alternating electrical signal suitable for powering the implantable device. For example, the antenna may output electromagnetic radiation which is not only strong enough to penetrate the body 130 in which the device 100 is implanted, but which also is strong enough to power and excite the implanted device 100. In this context, the strength of the electromagnetic radiation refers to the intensity of the radiation emitted by the antenna.

Although the antenna is shown as part of the reader device, in some circumstances it may be preferable to form the antenna as part of a garment or accessory, for example a brooch, necklace, bracelet, armband, hat, shirt or trousers. In this way, the patient can wear the antenna at all times, without inconveniencing themselves. When a reading is required, the patient simply needs to arrive at a location close to the reader device. A wired, wireless, or any other suitable connection may then be formed between the antenna and the reader device, and the implantable device can be operated as described herein. Embodiments of the present disclosure aim to provide continuous monitoring. Accordingly the reader and antenna may be worn on the body or carried in clothing. Reader and antenna can be integrated or separate, and/or joined by a cable. If only intermittent readings are wanted, the antenna and reader can be placed over the site of the implant for the duration. Communication with the implant itself is generally always wireless.

Although the implantable device is shown here implanted in a human or animal body, it is to be understood that the implantable device may be situated in any location in which in situ measurements are desirable, in particular in situ pressure measurements in hard to reach locations. For example applications may also exist in pipelines, engine cylinders, gas canisters, pumps or submersible equipment.

Figure 4:
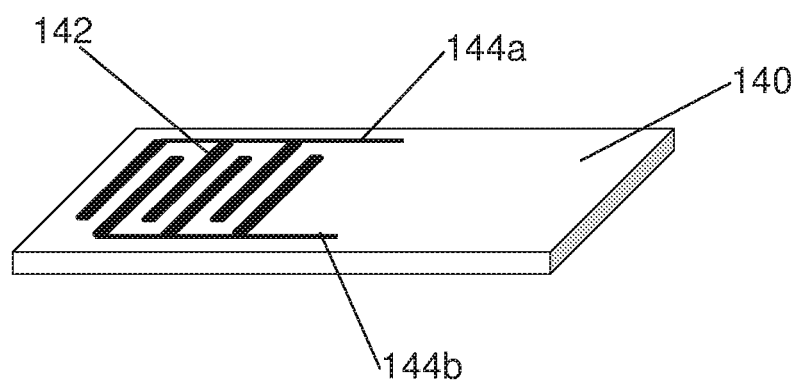
FIG. 4 is an illustration of an interdigitated transducer.

As an example of an IDT, consider FIG. 4. Here an IDT is shown mounted on a piezoelectric substrate 140. The IDT comprises a series of interlocked fingers 142 of a conductive material spaced apart from one another. In addition, connectors 144a and 144b link alternate interlocked fingers 142 together to from two interlocked comb shapes. In the event that a positive voltage is applied to e.g. a first one of the connectors 144a, relative to the other connector 144b, regions of the piezoelectric substrate 140 are caused to contract, while others may expand, due to the piezoelectric effect. If the voltage applied to the connectors 144 is now reversed, different areas now expand and contract. When the supplied signal is periodic, a surface acoustic wave (SAW) may be generated. To achieve this, the connectors 144a and 144b may be connected to a signal provider such as an antenna.

IDTs may be arranged to respond to a specific frequency band by choosing the spatial arrangement of the interlocked fingers. For example, the width of each finger, the separation between adjacent fingers, the length of each finger and/or the overlap between the two interlocking combs may all affect a resonance characteristic of an IDT, and consequently affect the frequency band to which that IDT responds. In an embodiment the membrane carrying the IDTs comprises quartz. Such embodiments may exhibit excellent temperature stability and high Q factor. The alignment of the transducer fingers (e.g. with respect to the crystal) and/or metallisation ratio of the IDTs (e.g. the ratio between the width of each finger and the spacing between fingers) and/or the metallisation thickness of the IDTs may be selected to provide a low (e.g. zero) temperature coefficient in the range of likely body temperatures e.g. 35° C. to 37° C. As an alternative to quartz, it is possible to use Aluminium nitride or Zinc Oxide piezoelectric films but the stability of the single-crystal quartz is better over the projected lifetime of the sensors (50 years possibly).

The flexing or deflection of the substrate 140 described above (e.g. due to pressure changes) will change the separation between the interlocked fingers 142 on the surface of the substrate 140. This change in separation will alter the frequency of a resonator or group delay of a delay device.

An acoustic wave may be instigated at the IDT by a stimulating radio frequency (RF) pulse received for example by an antenna from a source not shown external to the body (see e.g. FIG. 3). A second IDT may be used to receive this SAW, and convert it back to an electrical signal by a process which is effectively the reverse of the SAW generation process described above. Alternatively, a SAW reflector may be used to reflect the SAW back towards the IDT from which it originates. In this mode, the IDT operates as both a source and receiver. In either case, the electronic signal so generated by reception of a SAW by an IDT may be sent to an external device for further processing to determine properties of the environment in which the IDT is situated, e.g. local pressure. In a "delay-line" based device, this measurement may be based for example on the time delay between emission and receipt of a SAW, or in a "resonator" device the measurement may be based on a frequency shift introduced by the device.

Figure 5:
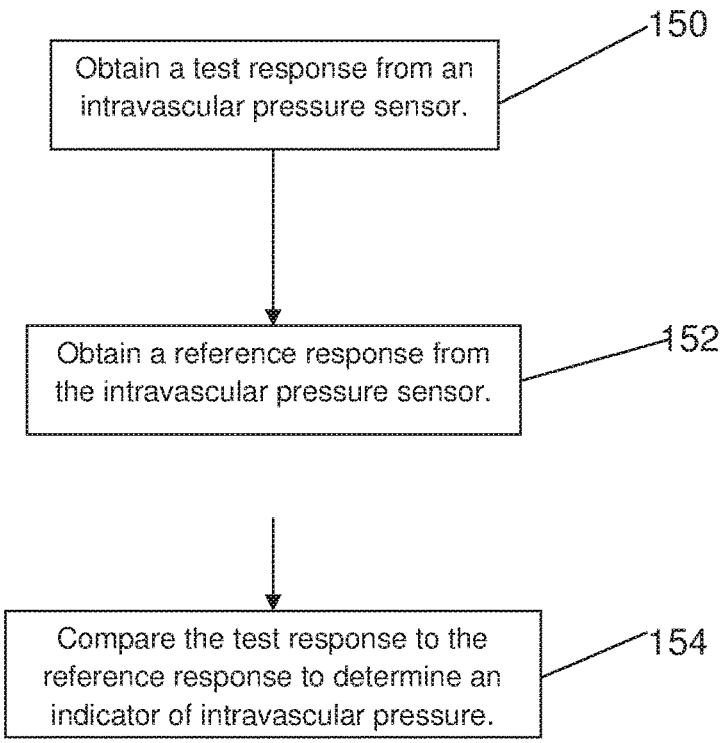
FIG. 5 is a flow chart describing the operation of the device.

Turning now to FIG. 5, the process for reading the intravascular pressure sensor is illustrated in a flow chart format. The method starts at step 150, wherein a test response is obtained from the intravascular pressure sensor. This involves the intravascular device receiving a test signal. For example, the test signal may comprise the emission of electromagnetic radiation, triggered by the controller and/or the reader device. The electromagnetic radiation emitted in this way has a frequency falling within a first frequency band.

When the implantable intravascular device receives the emitted test signal, it responds by emitting a test response. As described above, the test response is dependent on the external environmental conditions; in particular, the test response is dependent on the pressure in the region of the intravascular sensor. The test response may be emitted after a pressure-dependent time delay, or emitted at a frequency shifted from the frequency of the test signal, as described above. In the event that the frequency of the test response is shifted from the frequency of the test signal, the frequency of the test response may nonetheless fall within the first frequency band. For example, the test signal may have a wider bandwidth than the test response. The bandwidth of the test response may be encompassed by the bandwidth of the test signal. Alternatively, if the received test response is of low signal to noise ratio due to the frequency shift, the test signal may be varied to track the frequency shift to ensure that test response is of acceptable quality.

At step 152, the reference response is obtained from the intravascular pressure sensor. This involves the intravascular device receiving a reference signal. For example, the reference signal may comprise the emission of electromagnetic radiation, triggered by the controller and/or the reader device. The electromagnetic radiation emitted in this way has a frequency falling within a second frequency band.

When the implantable intravascular device receives the emitted reference response, it responds by emitting a reference response. As described above, the reference response is dependent on the external environmental conditions; in particular, the reference response is less dependent on the pressure in the region of the intravascular sensor. The reference response may be emitted after a pressure-dependent time delay, or emitted at a frequency shifted from the frequency of the reference signal, as described above. In the event that the frequency of the reference response is shifted from the frequency of the reference signal, the frequency of the reference response may nonetheless fall within the second frequency band. For example, the reference signal may have a wider bandwidth than the reference response. The bandwidth of the reference response may be encompassed by the bandwidth of the reference signal.

As described above the pressure dependence of the two responses may vary. For example, the test response may comprise a strong pressure dependence, while the reference response may comprise a weak pressure dependence. Indeed the reference response may even be pressure independent.

At step 154 the test response and the reference response are compared with one another, and an indicator of the pressure in the region of the device is determined from this comparison. This determination may use the fact that the reference response is less pressure dependent than the test response. By comparing the two results in this way, other factors which may have a similar effect on the readings can be controlled for. For example, increasing temperature may cause thermal expansion of the device, which in turn may cause the physical dimensions of the device to expand, and cause an increase in the time delay and/or affect the frequency response of the signal in a similar manner to the deflections due to pressure, described above. A comparison of the two readings can help to mitigate this effect.

In addition, the comparison may make use of other information. In particular, this additional information may include calibration information. For example, prior to implanting the intravascular device, the device may be calibrated by placing the device in a calibrator capable of supplying a controlled pressure environment.

A set of readings at various controlled pressures may be taken as part of the calibration process, and the corresponding reading may be noted at those pressures. For example, a calibration file may comprise a series of pressure readings correlated with an associated time delay and/or correlated with an associated frequency shift. The calibration may be repeated as often as necessary to ensure consistent, reproducible results are being obtained. When a test and reference reading are subsequently received, the calibration file can be used to help determine the pressure in the environment of the intravascular device. For example, the calibration file can be used as a look-up table, or it can form an input into a more complex calculation, depending on the specific application. For example, the calculation may involve one or more of: the known pressure of gas in a cavity; an independent temperature measurement; a stiffness or deflectability of one or more parts of the device; physical properties of the fluid surrounding the device (e.g. blood); speed of sound in parts of the device; and/or the physical arrangement of the conductive components which form the transducers.

In this way, the reference and test responses are used to control for variations in sensitivity of the intravascular device. In addition, changes in the test and reference responses which are not due to pressure may also be controlled for by the comparison, for example, variations may be due to changes in temperature.

Figure 6:
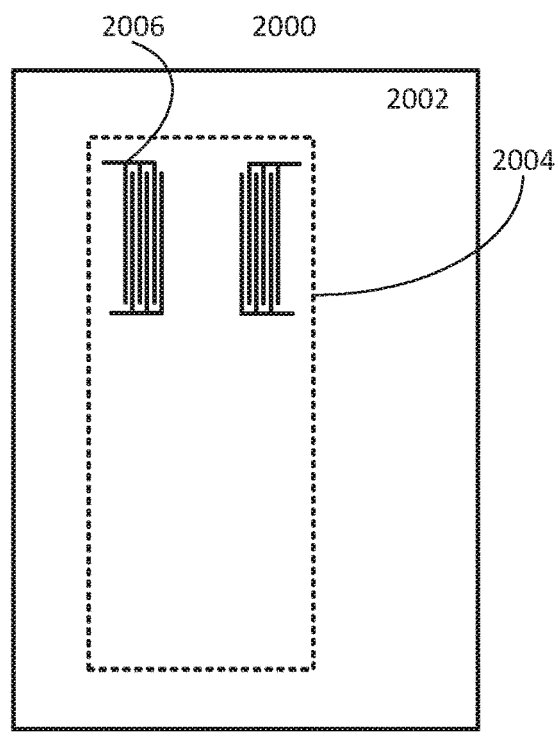
FIG. 6 shows an example of a transducer for providing enhanced sensitivity.

FIG. 6 illustrates a possible structure of a SAW transducer which can be used for implantable intravascular pressure sensors according to the present disclosure.

These transducers can be incorporated into other embodiments described herein, or they may be used independently. For example they may be used in any transducer which comprises a membrane substrate 2000, arranged over a cavity (such as cavity 112) comprising a fluid at a reference pressure so that deflection of the membrane is caused by variations in external fluid pressure (e.g. fluid pressure outside the membrane which covers the cavity).

Embodiments of the device illustrated in FIG. 6 comprise interdigitated transducers (IDTs) 2006, in which the conductive fingers of the IDTs are aligned in a first direction (referred to herein as the Y direction) for providing a surface acoustic wave propagating in a second direction (referred to herein as the X direction), transverse to that first direction.

A region 2004 substrate 2000 of the IDTs is arranged to be deflected by pressure changes (e.g. as described above) In addition, that substrate is also arranged so that, in the event that it is deflected the strain and/or stress in the substrate in the X-direction is greater than the stress in the Y direction. For example, depending on the size and shape of the device, the substrate membrane may be arranged so that stress in the X-direction is maximised (within the space constraints) and the stress in the Y-direction is minimised. This may provide enhanced sensitivity.

In more detail, the structure illustrated in FIG. 6 comprises at least one IDT arranged on an elongate rectangular region 2004 of a membrane 2000. This elongate rectangular region 2004 may be arranged over a cavity of fluid at a reference pressure so that it can be deflected by fluid pressure outside the cavity. For example, this cavity may be arranged as the cavity 112 described in relation to FIG. 1 and FIG. 2.

The fingers of the IDT 2006 are aligned with the longer edges of this rectangular region 2004 for providing a surface acoustic wave which propagates in a direction aligned with its shorter edges. Thus, a Y direction may be defined as the direction of the fingers, aligned with the long edges of the region, and an X direction may be defined as the direction of separation of adjacent fingers, which is aligned with the shorter edges. Accordingly, it can be seen that because of this alignment, if the region is deflected inward (compressing the fluid in the cavity) the stress and/or strain in the substrate in the X direction is increased whereas the stress in the Y direction is reduced.

The region may be rigidly supported at the edges of the region 2004, for example by hermetic bonds which secure it to the body of a sensing device which incorporates the cavity, e.g. as described above with reference to FIG. 1 and/or FIG. 2. As with other such SAW strain sensors, or pressure sensors using strain as part of the transduction process, this region can provide a beam or cantilever structure. The structure of the region (predominantly its shape, but other parameters could be used to do this) is chosen so that the strain and stress associated with this deflection are both predominantly in the same direction, perpendicular to the fingers of the IDTs.

The method steps described above may be performed by the reader device, or by another piece of equipment, and may be carried out by a dedicated piece of hardware, or a computer program, running on a computer system, for example a system comprising a processor coupled with a memory, or indeed it may be performed on any combination of these.

To the extent that certain methods may be applied to the living human or animal body, it will be appreciated that such methods may not provide any surgical or therapeutic effect. In addition, it will be appreciated that such methods may be applied ex vivo, to tissue samples that are not part of the living human or animal body. For example, the methods described herein may be practiced on meat, tissue samples, cadavers, and other non-living objects.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Any apparatus feature as described herein may also be provided as a method feature, and vice versa. Furthermore, equivalents and modifications not described above may also be employed without departing from the scope of the invention, which is defined in the accompanying claims.

In some examples, one or more memory elements can store data and/or program instructions used to implement the operations described herein. Embodiments of the disclosure provide tangible, non-transitory storage media comprising program instructions operable to program a processor to perform any one or more of the methods described and/or claimed herein and/or to provide data processing apparatus as described and/or claimed herein.

The activities and apparatus outlined herein may be implemented with fixed logic such as assemblies of logic gates or programmable logic such as software and/or computer program instructions executed by a processor. Other kinds of programmable logic include programmable processors, programmable digital logic (e.g., a field programmable gate array (FPGA), an erasable programmable read only memory (EPROM), an electrically erasable programmable read only memory (EEPROM)), an application specific integrated circuit, ASIC, or any other kind of digital logic, software, code, electronic instructions, flash memory, optical disks, CD-ROMs, DVD ROMs, magnetic or optical cards, other types of machine-readable mediums suitable for storing electronic instructions, or any suitable combination thereof.

What is claimed is:

1. An implantable intravascular pressure sensor comprising:
    a first transducer arranged to provide a pressure dependent signal in response to alternating electrical signals of a first frequency band;
    a second transducer arranged to provide a reference signal in response to alternating electrical signals of a second frequency band different from the first frequency band; and
    an antenna coupling for sending and receiving said signals, wherein the pressure dependence of the response provided by the first transducer is associated with deflection of a deflectable member by changes in intravascular pressure; and
    the reference response is associated with a reference member arranged to be deflected less than the deflectable member by those same changes in intravascular pressure;
    wherein the first transducer comprises a first interdigitated transducer, (IDT), on a surface of a piezoelectric crystalline substrate having a first crystal plane orientation, and
    the second transducer comprises a second IDT on the surface of the piezoelectric crystalline substrate having a second crystal plane orientation which is the same as the first crystal plane orientation.

2. The apparatus of claim 1, wherein the signals sent and received by the antenna coupling comprise radio frequency (RF) signals.

3. The apparatus of claim 2 wherein the antenna coupling sends and receives signals in a bandwidth which encompasses the first frequency band and second frequency band.

4. The apparatus of claim 1 wherein the different deflectability of the reference member and the deflectable member is associated with at least one of:
    (a) different thicknesses of the substrate; and
    (b) arrangement of support of the substrate.

5. The apparatus of claim 1 wherein the deflectable member is coupled to an enclosed cavity that provides a reference pressure in response to changes in intravascular pressure.

6. The apparatus of claim 1 wherein the deflectable member at least partially encloses said cavity, wherein the deflectable member is provided by a membrane, wherein the membrane has a thickness of less than 200 μm, or less than 60 μm, or more than 5 μm, or more than 10 μm, or more than 20 μm, or less than 100 μm.

7. The apparatus of claim 1 wherein the two transducers each comprise an assembly of conductive elements and the frequency band in which the transducers respond is selected by the spatial arrangement of said conductive elements.

8. The apparatus of claim 7 wherein the conductive elements are arranged to provide an LCR circuit.

9. The apparatus of claim 1, wherein the reference member and the deflectable member are provided by different regions of the same substrate.

10. The apparatus of claim 1, wherein the first IDT and the second IDT are surface acoustic wave (SAW) IDTs.

* * * * *